United States Patent [19]

Pelton et al.

[11] Patent Number: 4,745,909
[45] Date of Patent: May 24, 1988

[54] COLD MASSAGE TOOL AND METHOD OF USE THEREOF

[76] Inventors: Robert J. Pelton, P.O. Box 143, Nevada City, Calif. 95955; William M. Zulim, 9820 Tender Blossom Way, Stockton, Calif. 95209

[21] Appl. No.: 50,730

[22] Filed: May 15, 1987

[51] Int. Cl.$^4$ ............................................. A61F 7/10
[52] U.S. Cl. ................................. 128/24.1; 128/67; 128/62 R
[58] Field of Search ............... 128/24.1, 24.2, 399, 128/400, DIG. 27, 6 RR, 67

[56] References Cited

U.S. PATENT DOCUMENTS

| | | | |
|---|---|---|---|
| 1,744,423 | 1/1930 | Toadvine | 128/24.1 |
| 1,833,105 | 11/1931 | Aronson | 128/24.2 |
| 1,923,317 | 8/1933 | Lipsner | 128/399 |
| 2,378,087 | 6/1945 | Kearney | 128/399 |
| 3,804,077 | 4/1974 | Williams | 62/4 |
| 4,404,820 | 9/1983 | Romaine | 128/399 |

Primary Examiner—Edgar S. Burr
Assistant Examiner—Huong Q. Pham

[57] ABSTRACT

A cold massage tool. A closed tube of thin-walled heat-conductive material having one rounded end has an open end closed by a cap. A non-conductive heat-insulating tube open at both ends and shorter than the closed tube, encircles and tightly engages the closed tube from a point adjacent to the cap end and extending toward but well short of the rounded end, to provide a handle. A water-based material fills the closed tube. The water-based material can be frozen through a change-of-state condition by placing the tool in a freezing environment. It can thereafter be used to apply cold massage to a human body by bringing said rounded end into contact with a portion of the body, either directly or through a heat-conductive emollient gel. The contact may comprise gently massaging the gel-coated part in a continuous circular motion for five to seven minutes.

12 Claims, 1 Drawing Sheet

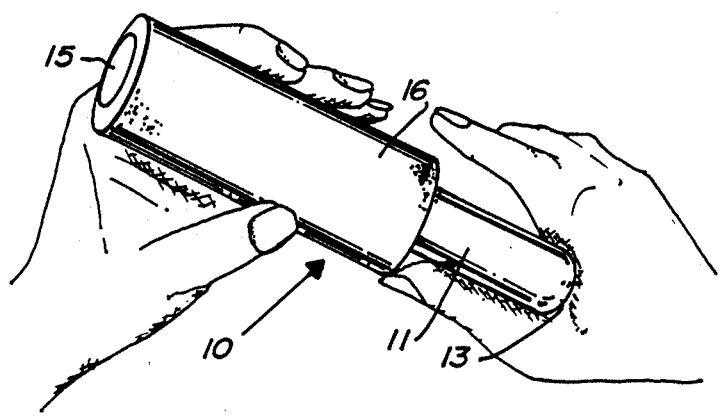
FIG. 1
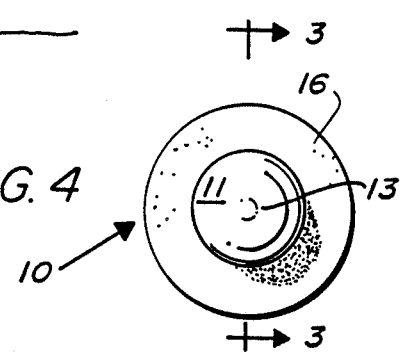
FIG. 4
FIG. 2
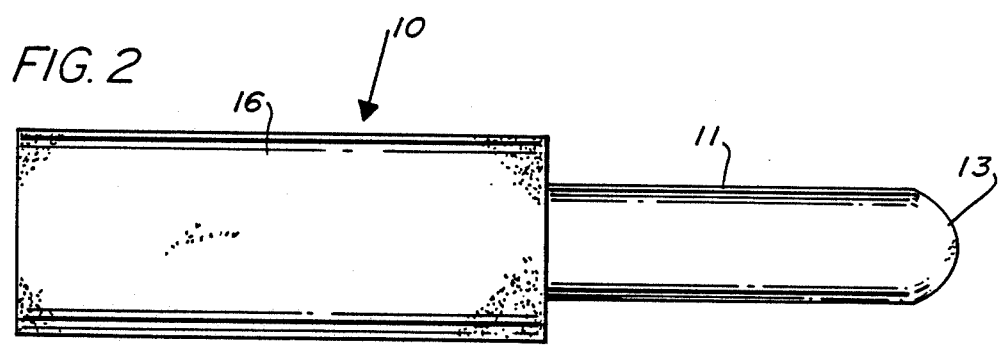
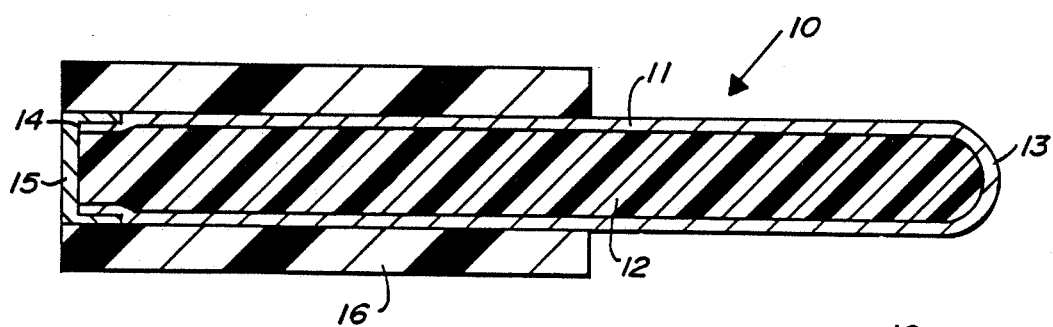
FIG. 3
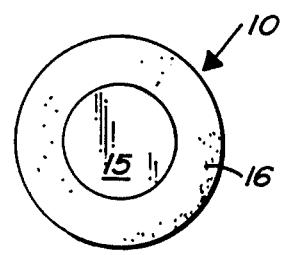
FIG. 5

COLD MASSAGE TOOL AND METHOD OF USE THEREOF

This invention relates to a cold massage tool and a method of using it.

BACKGROUND OF THE INVENTION

Ice massage is safe, effective, and inexpensive in controlling several kinds of pain. In sports medicine, it is used to relieve musculoskeletal aches and pains caused by strains and tension. Baseball pitchers typically put their pitching arm in a bucket of ice water after a game, to decrease ache and swelling and to prevent pains that might develop otherwise.

Why ice massage is effective has not been understood until recently, though it was known that it produces a local constriction of blood vessels, makes the area feel "numb" and it hurts, producing aching and burning pain. Recent studies suggest that it may act like acupuncture or intense transcutaneous electrical nerve stimulation (TENS).

In a study by Melzack et al. in 1980, patients suffering from acute dental pain were treated with ice massage of the back of the hand on the same side of the body as the pain, at what is known as the Hoku acupuncture point, located at the vertex of the web between the thumb and the index finger. The ice massage was found to halve the intensity of that dental pain for most patients, and to be more effective than tactile massage.

These observations led to another study by Melzack et al. in 1980, in which the relative effectiveness of ice massage and TENS were studied for the relief of low-back pain. These two methods were found to be about equally effective: about 65% of patients obtained pain relief greater than one-third. Ice massage was more effective than TENS for some patients, while TENS was more effective for others. Ice massage could be used as an additional sensory-modulation method, alternating with TENS to overcome adaptation effects.

In a further study by Melzack and Bentley in 1983, patients suffering acute dental pain were treated with ice massage of (1) the Hoku acupuncture point on the back of the hand, or (2) the lateral surface of the arm near the elbow. Four groups of patients received the ice massage at one of the points on the side ipsilateral or contralateral to the dental pain. A control group received tactile massage of the ipsilateral Hoku point. Changes in pain intensity produced by the procedure were measured by a McGill Pain Questionnaire. Pain intensity was significantly decreased by about 40-50% after ice massage of the ipsilateral hand, the contralateral hand or the contralateral arm. However, ice massage of the ipsilateral arm had no significantly better effect than tactile massage of the ipsilateral hand.

The effectiveness of ice massage of the contralateral hand is consistent with Chinese literature on acupuncture, which states that intense stimulation of certain points are particularly effective for relieving pain at or near distant sites.

Data demonstrate the importance of recognizing individual differences in the distribution of trigger or acupuncture points and the need to find them by careful exploratory palpation in each person.

The most common use of ice massage, however, is to apply the ice directly to the painful area. In the classic studies in this field, ice cubes held in gauze-pads or in a strip of cloth were moved thereon in a circular motion of the painful area.

An excellent review on "The Therapeutic Use of Cold" by Mennell (1975) describes the direct application of ice as well as the use of cold-sprays for "ice-and-stretch" treatment.

An earlier clinical study by Grant (1964), based on experience with more than 7000 outpatients, describes the use of direct application of ice for shoulder-neck pain, and low-back pain. Grant reported that initially the patient had a sensation of cold which tended to become more uncomfortable, and to be replaced by a burning sensation. In most patients, this was followed by an aching sensation for a short time. Massage was continued beyond this point to a state of analgesia and then discontinued. Then the patient was given a program of range of motion and mobilization exercises. If the pain relief was not enough to enable good patient performance in the exercise program, the ice massage was repeated. Such a second period of icing was rarely required, but at times even a third application was given.

For most areas the ice massage took from five to seven minutes. Areas with considerable fatty subcutaneous tissue required a longer period of icing. Very thin patients commonly required a shorter icing period and tended to complain more about discomfort, but they also tended to show the best clinical results.

A later study by Kirk and Kersley (1968) examined the relative effectiveness of "heat and cold in the physical treatment of rheumatoid arthritis of the knee" and reported that no applications of crushed ice in a damp towel "were acceptable to patients and were associated with a greater relief of pain and stiffness than hot applications." However, both were equally effective on objective measurements of movement.

Other studies (Halliday Pegg et al., 1969; Stangel, 1975) reported efficacious results for arthritic and other pains.

A discovery, based on clinical observation, was made in the 1930's by Janet Travell (who later became President John F. Kennedy's personal "Physician in the White House"). Dr. Travell discovered that many severe musculoskeletal pains were associated with localized spots—"trigger points"—which were highly sensitive to touch. When pressure was applied to the spots, they evoked pain in a distinct area which usually surrounded the spot or was near it but might be at a considerable distance away. Beneath the trigger point, palpation often revealed a band of muscle in spasm. Dr. Travell found that by "dry needling" the spot or by applying a cold spray,.it became possible to relieve the pain of the trigger spot as well as the pain in the larger area of referred pain. Thus, stimulation of trigger points by a variety of inputs appears to be capable of relieving pain.

This area of investigation led to the hypothesis by Melzack in 1975 and 1977 that acupuncture points and trigger points actually represent the same physiological phenomenon. To test this hypothesis, Melzack, Stillwell and Fox (1977) examined the distribution of both sets of points (and the related areas of pain) and found an astonishingly close correspondence—71%—between them. This close correlation suggests that trigger points and acupuncture points for pain, though discovered independently and labelled differently, represent the same phenomenon and can be explained in terms of similar underlying neutral mechanisms.

These results suggest that ice massage, which is an extremely simple procedure, can be used for a variety of clinical pain problems. A patient can, for example, easily be shown how to rub ice over the appropriate areas of the hand to diminish toothache.

The fact that intense inputs of almost any kind tend to diminish pain had led to the labelling of this phenomenon as hyperstimulation analgesia; that is, relief of pain by intense (sometimes painful) stimulation.

The mechanisms for the effects of ice massage appear to lie at several levels:

1. Ice massage produces a local constriction of blood vessels and consequently may diminish swelling, decrease local bleeding after an injury, and may slow down the release of bradykinin, histamine and other pain-eliciting substances.

2. Interaction among fibers of different sizes at the level of the dorsal horn of spinal cord have been extensively documented (see Melzack and Wall, 1983; Wall, 1984).

3. Areas in the brainstem can exert an inhibitory control over transmission.

With all these desirable qualities, still it must be admitted that ice cubes, crushed ice, and cloth-wrapped ice are all awkward to use, and difficult to handle. When the ice melts, it gets everything wet that it melts on or through. The present invention is directed toward obtaining the beneficial effects of ice massage in a much more convenient manner. It enables use of cold massage with a simple and effective tool.

SUMMARY OF THE INVENTION

The invention provides a cold massage tool, comprising a closed tube of thin-walled heat-conductive material having one rounded end and one initially open end closed by a cap, a non-conductive heat-insulating tube open at both ends, shorter than the closed tube and encircling and tightly engaging the closed tube from the cap end and extending toward but well short of the rounded end. A water-based material fills the closed tube.

This water-based material can be frozen through a change-of-state condition by placing the tool in a freezing environment (such as a freezer). It can thereafter be used to apply cold massage to a human body by bringing the rounded end into contact with a portion of the body directly or through a heat conductive gel.

The water-based material may be a water gel, preferably containing a preservative, or may be water containing a dissolved material of the type lowering the freezing point relative to that of water.

The closed tube may be made of aluminum or stainless steel, and the insulating tube may be made from a spongy elastomer, such as foamed polyurethane or a synthetic sponge rubber.

BRIEF DESCRIPTION OF THE DRAWINGS

FIG. 1 is a view in perspective of a tool embodying the principles of the invention. A pair of hands are also shown, with the tool being held in one hand and its rounded end being applied to a portion of the other hand, i.e., to the Hoku acupuncture point.

FIG. 2 is a view in side elevation of the tool shown in FIG. 1.

FIG. 3 is a view in longitudinal section of the took, taken along the line 3—3 in FIG. 4.

FIG. 4 is a view in end elevation looking at FIG. 2 from the right.

FIG. 5 is an end elevation looking at FIG. 2 from the left.

DESCRIPTION OF A PREFERRED EMBODIMENT

A tool 10 embodying the principles of the invention is shown in the drawings. It comprises a closed tube or receptacle 11, preferably of aluminum or stainless steel. It is thin-walled and of heat conductive material. The tube 11 is filled with a material 12 which serves to retain cold well. The tube 10 preferably is provided with a rounded end 13 and an open end 14 which is closed by a metal cap 15, preferably of the same material as the tube 11 and is welded or cemented to it to seal the material 12 inside. Around approximately half the length of the tube 11 and preferably a little more is a handle member 16 comprising an open-ended tube of an insulating grip material, such as a sponge rubber or synthetic elastomer foam such as a nitrile vinyl polymer or a somewhat foamed polyurethane, a compressible material. This may be cemented to the tube 11 or may simply grip it frictionally.

The material 12 inside the tube may simply be water, but improved results can be obtained by using a gel which is made from starch and water, usually being provided with a preservative or bactericide material to prevent organic action due from the starch. The gel has a good ability to absorb heat. The gel may contain a salt or other material to adjust the freezing point.

The material may instead be a solution of a salt (sodium chloride or sulfate) in water in quantities to provide a selected freezing point or a mixture of water and methylene glycol or any other anti-freezong agent as a freezing depressant. This enables the use of different freezing points.

In use, the tool 10 is placed into a freezer and the material inside the container is thereby frozen. When ready, the rounded end 13 is applied in place of ice to obtain the desired results. Preferably, the part of the body to which such tool 10 is applied is first anointed with a heat-conductive emollient gel. The gel may be a gel comprising aloe vera in deionized water contaianing propylene glycol, and panthenol. It may also contain vitamins and other emollients. The gel may be spread over the desired area fairly thickly. The tool 10 is preferably not pressed hard against the skin but the rounded end 13 is used to massage the areas gently, preferably in a continuous circular motion for about five to seven minutes, and in any event no more than 10 minutes.

To those skilled in the art to which this invention relates, many changes in construction and widely differing embodiments and applications of the invention will suggest themselves without departing from the spirit and scope of the invention. The disclosures and the descriptions herein are purely illustrative and are not intended to be in any sense limiting.

What is claimed is:

1. A hand-held cool massage tool for applying pressure to traditional accupressure points, comprising:
   a closed, tube of thin-walled aluminum or stainless steel having one rounded end and one open end closed by a cap,
   a non-conductive heat-insulating and anti-slipping tube open at both ends and shorter than said closed tube, encircling and tightly engaged with said closed tube from a point adjacent to said cap end and extending toward but well short of said rounded end, to provide a handle, and a water-based material filling said closed tube, whereby said water-based material can be frozen through a change-of-state condition by placing said tool in a freezing environment, the tool thereafter being used to apply pressure at cold temperatures to traditional acupressure points on a human body by bringing said rounded end into contact, with pressure, on said pressure points.

2. The tool of claim 1 wherein said water-based material is a water gel.

3. The tool of claim 2 wherein said gel contains a freezing-point depressant.

4. The tool of claim 2 wherein said gel is a starch-water gel containing a starch preservative for preventing organic degradation.

5. The tool of claim 1 wherein said water-based material is water, containing a dissolved freezing-point depressant.

6. The tool of claim 1 wherein said insulating tube is made from a spongy elastomer.

7. The tool of claim 6 wherein said insulating tube is made of foamed polyurethane.

8. The tool of claim 6 wherein said insulating tube is made of a synthetic sponge rubber.

9. A method for cold-treating a portion of a human body, comprising providing a constant diameter cylindrical tool having a closed aluminum or stainless steel tube with a lower rounded end and an upper capped end filling said tube with a water-based starch gel and encircling said tube above said rounded end with an insulating handle, and treating a selected body portion by placing said tool in a freezing environment until said water-based material is frozen, removing said tool from said environment and, contacting and exerting pressure with said rounded end against a chosen part of the human body, while holding said tool by said handle.

10. The method of claim 9 wherein before said contacting and exerting pressure step, there is a step of applying a heat-conductive emollient gel to the chosen part.

11. The method of claim 9 wherein said contacting and exerting pressure step is done by gently massaging the gel-coated part in a continuous circular motion for five to seven minutes.

12. A hand-held cold massage tool for applying pressure to traditional accupressure points, comprising:

a closed cylindrical, constant diameter tube of thin walled aluminum or stainless steel having one rounded end and one open end, said open end being closed leak-tight by a stainless steel or aluminum cap, a non-conductive heat-insulating foamed polyurethane tube open at both ends and shorter than said closed tube, encircling and tightly engaged with said closed tube from a point adjacent to said cap end and extending toward but well short of said rounded end, to provide a handle, and a water-based starch-water gel uniformly filling said closed tube, whereby said water-based material can be frozen through a change-of-state condition by placing said tool in a freezing environment, the tool thereafter being used to apply pressure at cold temperatures to traditional acupressure points of a human body by holding said polyurethane tube in one hand and bringing said rounded end into contact with and exerting pressure on a portion of said body.

* * * * *